(12) United States Patent
Sauer (10) Patent No.: US 11,399,820 B2
(45) Date of Patent: Aug. 2, 2022

(54) MINIMALLY INVASIVE SUTURE PLACEMENT SYSTEM AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 278 days.

(21) Appl. No.: 16/380,956

(22) Filed: Apr. 10, 2019

(65) Prior Publication Data
US 2019/0298337 A1    Oct. 3, 2019

Related U.S. Application Data

(63) Continuation-in-part of application No. 16/367,781, filed on Mar. 28, 2019.

(60) Provisional application No. 62/655,656, filed on Apr. 10, 2018, provisional application No. 62/649,528, filed on Mar. 28, 2018.

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0482* (2013.01); *A61B 17/0487* (2013.01); *A61B 17/0057* (2013.01); *A61B 17/0491* (2013.01); *A61B 17/06066* (2013.01)

(58) Field of Classification Search
CPC .......... A61B 2017/048; A61B 17/0469; A61B 17/3423
See application file for complete search history.

(56) References Cited

U.S. PATENT DOCUMENTS

| | | | |
|---|---|---|---|
| 2006/0052802 A1* | 3/2006 | Sterman | A61F 2/2427 606/148 |
| 2015/0216514 A1* | 8/2015 | Weisbrod | A61B 17/3421 606/232 |

* cited by examiner

*Primary Examiner* — Wade Miles
*Assistant Examiner* — Mohammed S Adam
(74) *Attorney, Agent, or Firm* — Michael E. Coyne (57) ABSTRACT

A suture placement system is disclosed. The suture placement system has a plate defining a first opening spaced from a second opening. The suture placement system also has a first lumen having proximal and distal ends, wherein the distal end of the first lumen is coupled to the first opening. The suture placement system further has a second lumen having proximal and distal ends, wherein the distal end of the second lumen is coupled to the second opening. The suture placement system also has a guide coupled to the plate. A method of minimally invasive suture placement is also disclosed.

12 Claims, 9 Drawing Sheets

MINIMALLY INVASIVE SUTURE PLACEMENT SYSTEM AND METHODS THEREOF

RELATED APPLICATIONS

This application is a Continuation-in-Part of U.S. patent application Ser. No. 16/367,781 filed Mar. 28, 2019 and entitled, MINIMALLY INVASIVE SUTURE PLACEMENT SYSTEM AND METHODS THEREOF". The Ser. No. 16/367,781 application claims priority to U.S. Provisional Patent Application No. 62/649,528 filed Mar. 28, 2018 and entitled, "MINIMALLY INVASIVE SUTURE PLACEMENT SYSTEM AND METHODS THEREOF", and the current application claims that priority benefit as well. The current application also claims priority to U.S. Provisional Patent Application No. 62/655,656 filed Apr. 10, 2018 and entitled, "MINIMALLY INVASIVE SUTURE PLACEMENT SYSTEM AND METHODS THEREOF". The Ser. No. 16/367,781, the 62/649,528, and the 62/655,656 applications are also hereby incorporated by reference in their entirety.

FIELD

The claimed invention relates to surgical devices, and more specifically to suture placement systems for use in minimally invasive surgeries.

BACKGROUND

Modern advances in cardiac surgery have made it possible to repair or replace heart valves using minimally invasive surgical techniques. As minimally invasive techniques have improved, surgeons have been able to operate on patients through smaller and smaller access holes, resulting in less perioperative pain and shorter recovery times. A main focus of innovation in minimally invasive cardiac surgery has been on automated suturing technology for placement of suture stitches through tissue and also through the sewing cuffs of prosthetic devices such as, for example, annuloplasty rings. For example the RAM® Device, sold by LSI Solutions, Inc. of Victor, N.Y. (www.lsisolutions.com), is particularly effective for the automatic placement of pledgeted sutures in tissue, such as an aortic annulus during minimally invasive aortic valve surgery. The RAM® Device may be used in conjunction with a SEW-EASY® Device, also sold by LSI Solutions, Inc., for the automated placement of those same sutures through a sewing cuff of a prosthetic heart valve or an annuloplasty ring. By utilizing such automated suturing tools, surgeons are able to accomplish most of their surgical actions through very small incisions (on the order of 5 cm) made in one of the intercostal spaces between a patient's ribs. This is particularly beneficial to the patient, as the previous alternatives were much larger openings, including the use of a full sternotomy. Minimally invasive surgery is less traumatic to patients and often enables them to be on cardio-pulmonary bypass (CPB) machines for shorter times, thereby improving patient outcomes and reducing recovery times.

While more steps continue to be taken to reduce the amount of time a patient must be on CPB, surgeons continue to push the boundaries of what is possible by striving to be able to perform certain surgeries on a beating heart without the need for CPB. It would be even more desirable to be able to perform specific cardiac surgical procedures on a beating heart under minimally invasive conditions. For example, it would be highly desirable to be able to perform a tricuspid valve repair through a cannula placed between a patient's ribs and into the right atrium of the heart while the heart is still beating. The pressure in the right atrium is such that the blood would tend to fill partially into such a cannula, and of course, there would be blood within the right atrium which would also, unfortunately, completely obscure a surgeon's view of the right atrium and the tissues of the tricuspid valve if such an approach were to be taken. Even echocardiography, on its own, would have a difficult time allowing the surgeon to orient a suturing device through the blood field for a series of related stitches. Therefore, it would be desirable to have a minimally invasive suture placement system and method which would enable reliable suture placement around a cardiac valve, such as a tricuspid valve, even under conditions of zero direct and zero endoscopic visibility to enable minimally invasive beating heart surgery for better patient outcomes.

SUMMARY

A suture placement system is disclosed. The suture placement system has a plate defining a first opening spaced from a second opening. The suture placement system also has a first lumen having proximal and distal ends, wherein the distal end of the first lumen is coupled to the first opening. The suture placement system further has a second lumen having proximal and distal ends, wherein the distal end of the second lumen is coupled to the second opening. The suture placement system also has a guide coupled to the plate.

A method of minimally invasive suture placement is also disclosed. A minimally invasive suturing device is used to place a stitch of a first implant suture in tissue. A first end of the implant suture is pulled through a second lumen coupled to a plate. The first end of the implant suture is secured relative to the second lumen such that a distal end of the second lumen is held against the tissue. A second end of the implant suture is secured relative to a first lumen such that a distal end of the first lumen is held against the tissue. A follower on the minimally invasive suturing device is slid down a guide coupled to the plate at a fixed spacing from at least one of the first and second lumens until a tissue bite area of the suturing device coupled to the follower contacts the tissue. A stitch of a second implant suture is placed into the tissue at a position determined at least in part by an arc which the minimally invasive suturing device is able to follow by having the follower pivot on the guide.

BRIEF DESCRIPTION OF THE DRAWINGS

The claimed invention relates to surgical devices, and more specifically to suture placement systems for use in minimally invasive surgeries.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1A:
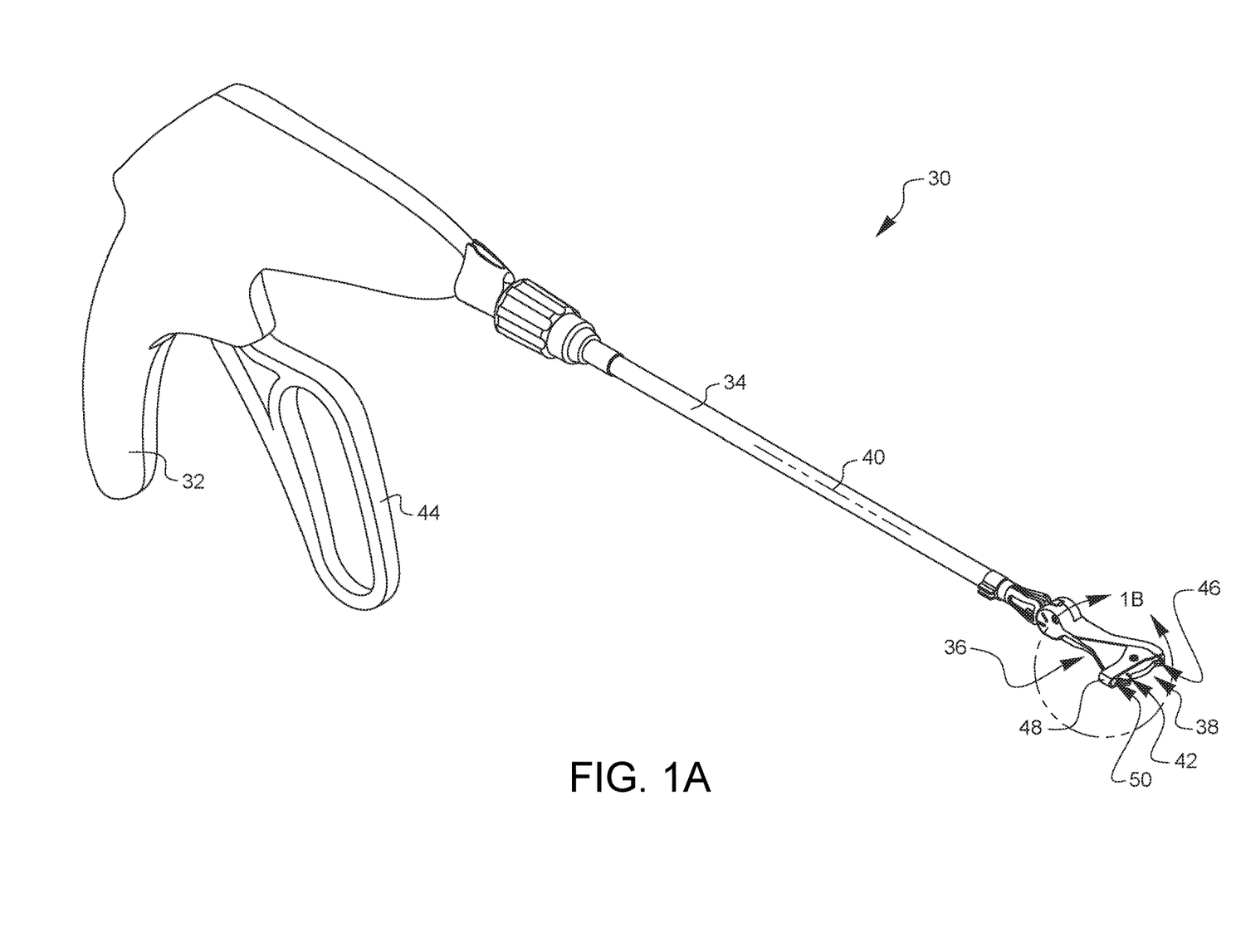
FIG. 1A illustrates one embodiment of a minimally invasive suturing device.

FIG. 1A illustrates one embodiment of a minimally invasive suturing device 30. The suturing device 30 has a handle 32 from which a shaft 34 extends. A distal sewing tip 36 resides at the end of the shaft 34. This particular suturing device 30 has an arcuate tissue bite area 38 facing distally along the longitudinal axis 40 of the suturing device 30. Although not shown in this view, an implant suture (for tissue implantation) with a ferrule on at least a first end of the implant suture may be loaded into the device 30 such that the ferrule on the end of the suture (not shown in this view) is held by a ferrule holder 42 in the device tip 36. In operation, a surgeon uses the handle 32 to manipulate the tissue bite area 38 against tissue where a suture stitch is desired. A lever 44 is then squeezed to actuate a needle (not visible in this view) to exit an opening 46 in the device tip 36, traverse through the tissue in the tissue bite area 38, and move into contact with the ferrule stored in the ferrule holder 42. The contact of the needle with the ferrule causes the ferrule to become attached to the needle, and when the surgeon releases the handle 44, the needle (with its attached ferrule) retracts back through the tissue in the tissue bite area 38 while also pulling the attached implant suture through the tissue. Thus, a suture stitch is formed in the tissue. This manner of using a needle with a ferrule for suturing is known to those skilled in the art, and a variety of needle configurations, including, but not limited to single needle devices, multiple needle devices, curved needle devices, and straight needle devices are compatible with the claimed invention. For simplicity, only a single suturing device 30 is discussed as an example.

Figure 1B:
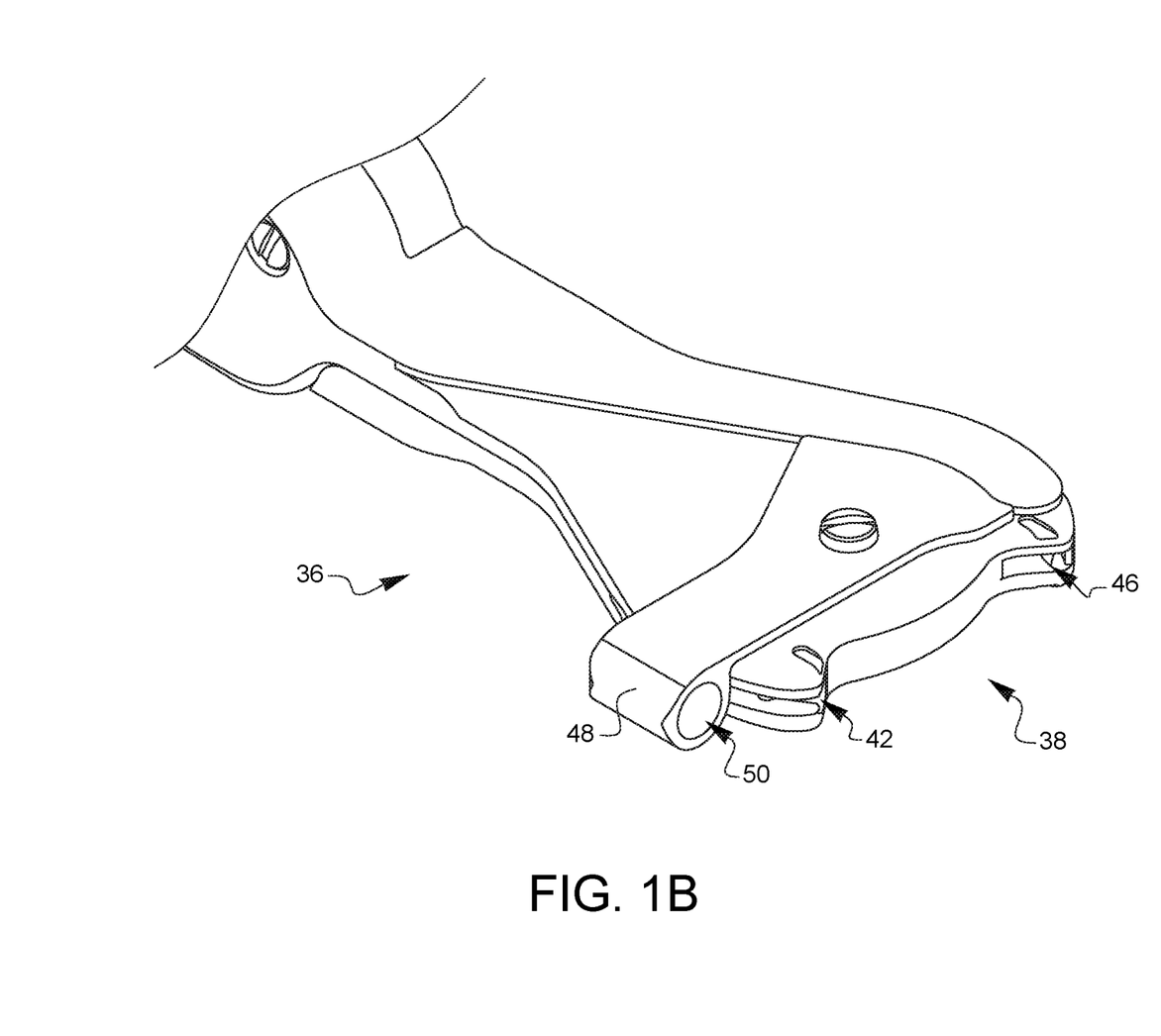
FIG. 1B is an enlarged view of the device tip of the minimally invasive suturing device of FIG. 1A.

A novel feature on the device tip 36 of this embodiment is a follower 48 coupled to the minimally invasive suturing device 30. The follower 48 defines an opening 50 which can be seen in the enlarged view of the device tip in FIG. 1B which is configured for slideable engagement with a guide (not visible in this view, but the guide is discussed in more detail with regard to the suture placement system embodiments below).

Figure 2:
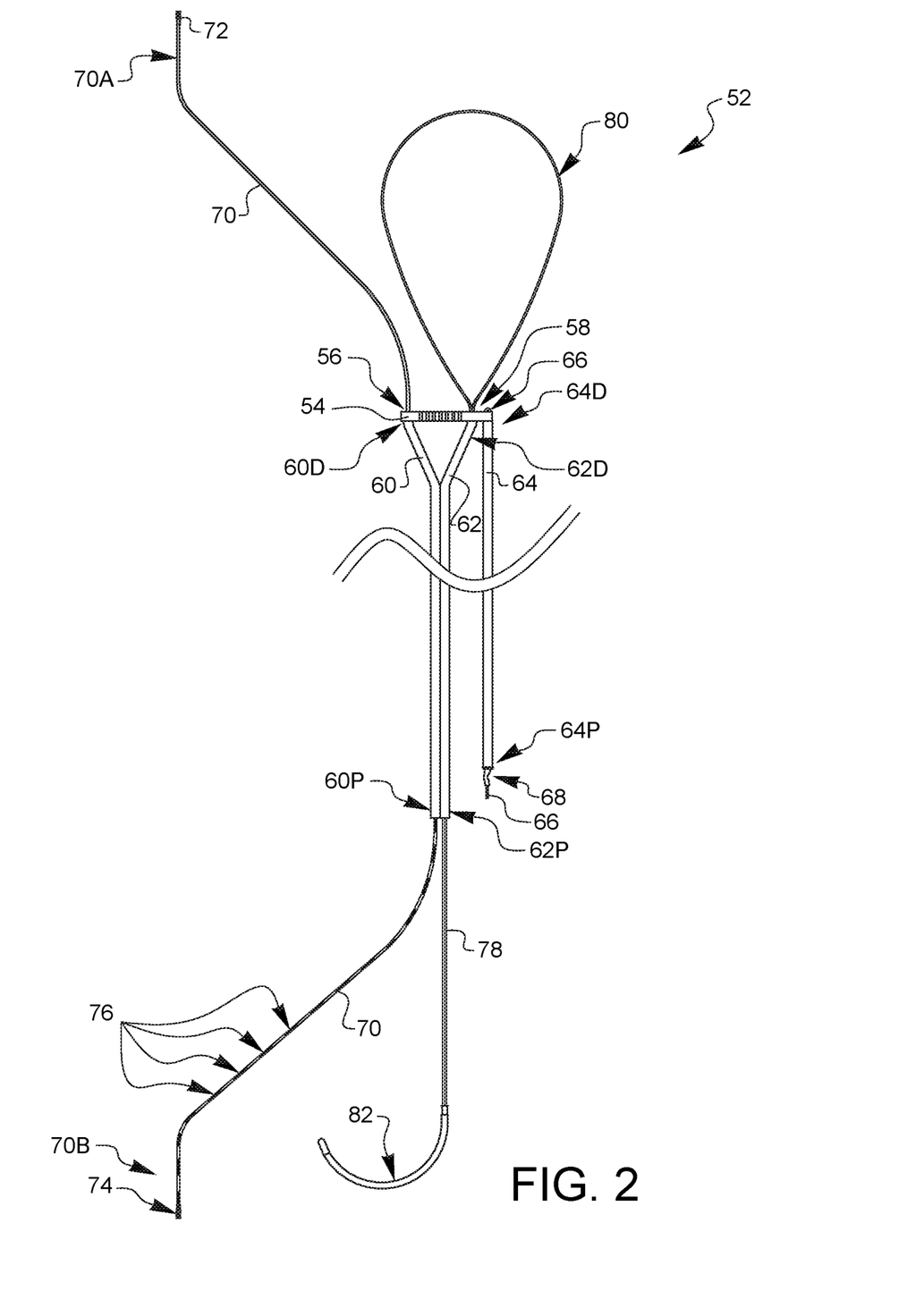
FIG. 2 illustrates one embodiment of a suture placement system.

FIG. 2 illustrates one embodiment of a suture placement system 52. The suture placement system 52 has a plate 54 defining a first opening 56 which is spaced from a second opening 58. The suture placement system 52 has a first lumen 60 having a proximal end 60P and a distal end 60D.

The distal end 60D of the first lumen 60 is coupled to the first opening 56 in the plate 54. The suture placement system 52 also has a second lumen 62 having a proximal end 62P and a distal end 62D. The distal end 62D of the second lumen 62 is coupled to the second opening 58 in the plate 54. A guide 64 is also coupled to the plate 54.

In this embodiment, the second opening 58 is located between the first opening 56 and the point where the guide 64 is coupled to the plate 54. Also in this embodiment, the guide 64 is a tube which is removably coupled to the plate 54 by an attachment suture 66 that engages the plate 54, passes through the distal end 64D of the guide tube 64, and is secured near a proximal end 64P of the guide tube 64 by a fastener 68 to keep the guide tube 64 coupled to the plate 54. One non-limiting example of a suitable fastener 68 is a crimpable titanium knot, such as the Ti-KNOT® fastener from LSI Solutions, Inc of Victor, N.Y. (www.lsisolutions.com). If it is ever desired to remove the guide 64 from the plate 54, the fastener 68 just has to be cut from the attachment suture 66 and the tube will release. In other embodiments, the guide 64 could be coupled to the plate 54 using other techniques, including, but not limited to gluing, ultrasonic welding, or simply fabricating both parts from a single continuous piece of material. The guide 64 may have a variety of cross-sectional shapes, including, but not limited to circular, oval, square, rectangular, triangular, notched, and keyed.

The follower 48 described in FIG. 1 is configured for slideable engagement with the guide 64 of FIG. 2. As such, the opening 50 defined by the follower 48 should have a shape which is compatible for slideable engagement with the guide 64. In embodiments where the guide 64 comprises a fastener 68, the opening 50 of the follower 48 should be sized to fit over the fastener 68 before going onto the guide 64. In other embodiments, the opening 50 may comprise a partially closed opening which can be set against the guide 64 without needing to pass over the fastener 68.

In the embodiment of FIG. 2, a portion of the first and second lumens 60, 62 are bonded together. As will be noted later in this discussion, respective ends of an implantation suture will be exiting the proximal ends 60P, 62P of the lumens 60, 62. By having the first and second lumens 60, 62 bonded together, especially at the proximal ends 60P, 62P, a single clamp may be used to grip the lumens 60, 62 to hold the suture ends in place. In other embodiments, the first and second lumens 60, 62 may not be bonded together at all, but could be separate. In still other embodiments, at least a portion of the first and second lumens may be housed within the same suture tube.

The suture placement system 52 also has an implant suture 70 having a first ferrule 72 on a first end 70A of the implant suture 70. The implant suture 70 also has a second ferrule 74 on a second end 70B of the implant suture 70. The implant suture 70 is partially located within the first lumen 60 such that the first end 70A of the implant suture 70 with the first ferrule 72 extends from the distal end 60D of the first lumen 60. The second end 70B of the implant suture 70 with the second ferrule 74 extends from the proximal end 60P of the first lumen 60. In this embodiment, the implant suture 70 has one or more markings 76 to differentiate the second end 70B from the first end 70A of the implant suture 70.

The suture placement system 52 also has a snare 78 having a snare loop 80 and a snare handle 82. The snare 78 is at least partially located within the second lumen 62 such that at least a portion of the snare loop 80 extends from the distal end 62D of the second lumen 62, while at least a portion of the snare handle 82 extends from the proximal end 62P of the second lumen 62. Depending on the embodiment, the snare handle 82 does not have to be a separate piece from the wire, suture, or other material which forms the snare loop 80. The snare handle 82 could simply be the ends of the material which forms the snare loop 80.

Figure 3:
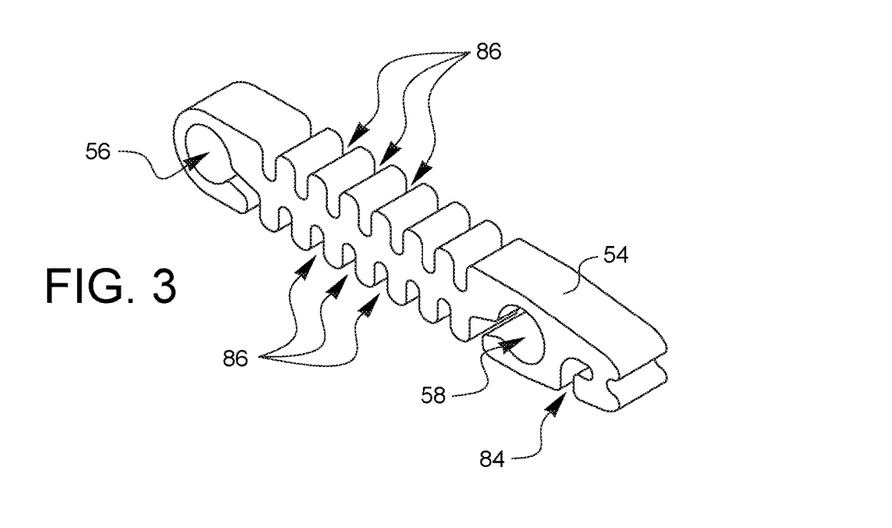
FIG. 3 is a proximal-top-right perspective view of one embodiment of a plate which is part of the suture placement system of FIG. 2.
Figure 4A:
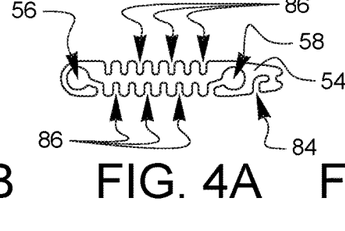
FIGS. 4A, 4B, 4C, 4D, 4E, and 4F are proximal, left, right, distal, top, and bottom elevational views, respectively, of the plate 54 from FIG. 3.
Figure 4B:
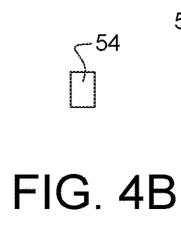
Figures 4C, 4D:
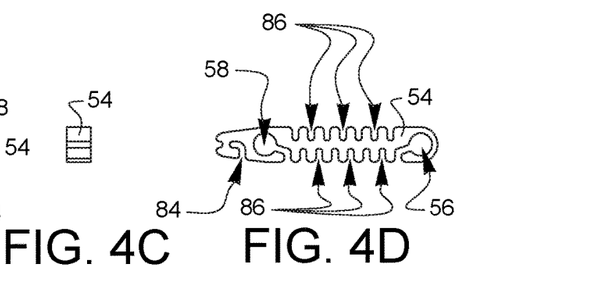
Figure 4E:
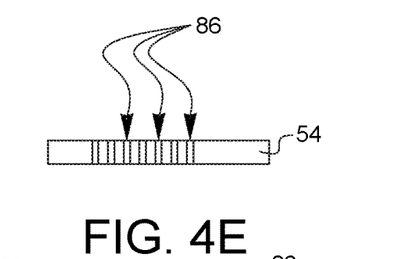
Figure 4F:
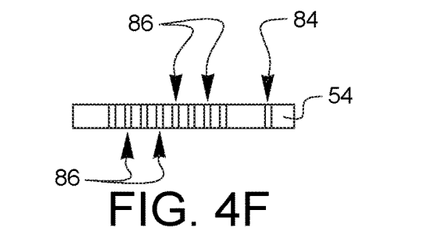

FIG. 3 is a proximal-top-right perspective view of one embodiment of the plate 54 discussed above as part of the suture placement system. The first and second openings 56, 58, where the first and second lumens (not shown in this view), respectively, are coupled to the plate, are visible in this view. An attachment feature 84 for the guide 64 (not shown in this view) is also defined by the plate 54. The attachment suture 66 may be threaded around this attachment feature 84 and held in place as described above. In this embodiment, the plate 54 has surface variations 86 which are configured to make the plate visible on an echocardiogram. In this example, the surface variations 86 take the form of notches, but other embodiments could have other shapes for surface variations, including no surface variations at all. The suture placement system is intended to be used in a beating heart where blood will likely obscure the distal portions of the system (including the plate) from being seen with the naked eye, loops, or an endoscope. It will be advantageous to be able to see the system on an echocardiogram, so if surface variations are not used, it may be desirable in some embodiments to coat at least a portion of the plate with a coating configured to make the plate visible on an echocardiogram. Such coatings are known to those skilled in the art. Such coatings could also be used in combination with surface variations 86. Furthermore, one or more of the plate 54, the first lumen 60, the second lumen 62, and the guide 64 may have a coating configured to make these parts visible on an echocardiogram. Additionally, it may be desirable to add such coatings to the follower 48 on the suturing device 30 and/or the distal tip 36 of the suturing device 30.

FIGS. 4A, 4B, 4C, 4D, 4E, and 4F are proximal, left, right, distal, top, and bottom elevational views, respectively, of the plate 54 from FIG. 3.

With reference to the devices above, in practice, the first ferrule 72 on the first end 70A of the implant suture 70 is loaded into the ferrule holder 42 of the minimally invasive suturing device 30. The remainder of the suture placement system 52 may be held nearby the suturing device 30 while the tissue bite area 38 is positioned against a desired tissue. For an example, we will say the tissue bite area 38 is positioned against a portion of the annulus of a tricuspid valve during a minimally invasive beating heart surgery. Using echocardiography a surgeon should be able to position the tissue bite area 38 appropriately on the annulus, especially if some feature on the distal tip 36 is configured to make it echo-visible. The difficulty comes in trying to place subsequent stitches in appropriate relation to the first stitch of the implant suture. The claimed invention, and its equivalents, provide a novel solution for this difficulty.

After the first implant suture 70 is stitched through the annulus, the suturing device 30 is removed from the blood field and the first ferrule 72 is released from the suturing device. The first end 70A of the implant suture 70 is pulled through the second lumen 62 by placing the first end 70A in the snare loop 80 and pulling it proximally through the second lumen 62 with the handle 82. The distal end 62D of the second lumen 62 and/or the second opening 58 in the plate 54 can be positioned against the tissue and the first end 70A of the implant suture 70 may be secured relative to the second lumen 62, for example, by placing a mosquito or other suitable clamp on the proximal end 62P of the second lumen 62. As configured in the embodiment of FIG. 2, the second end 70B of the implant suture 70 is already passed through the first lumen 60. If this was not the case, an embodiment could be provided with a separate snare for pulling the second end 70B of the implant suture 70 through the first lumen 60. In our example, however, the second end 70B is already through the first lumen 60. The second end 70B of the implant suture 70 may then be secured relative to the first lumen 60 such that the distal end 60D of the first lumen 60 and/or the first opening 56 in the plate 54 can be positioned against the tissue and the second end 70B of the implant suture 70 may be secured relative to the first lumen 60, for example, by placing a mosquito or other suitable clamp on the proximal end 60P of the first lumen 60. Alternatively, a single clamp may be used on the proximal ends 60P, 62P of the first and second lumens 60, 62 after the suture placement system is positioned against the tissue. In other embodiments, one or more integrated suture locks may come coupled to the proximal ends 60P, 62P of the first and/or second lumens 60, 62.

With the suture placement system 30 held in place against the tissue, a second implant suture 88 is then loaded into the distal tip 36 of the suturing device, and the opening 50 of the follower 48 is placed over the guide 64 of the suture placement system 52 which is being held in position against the tissue. The follower 48 on the minimally invasive suturing device may then be slid down the guide 64 coupled to the plate 54 until the tissue bite area 38 of the suturing device coupled to the follower 48 contacts the tissue. Since the guide 64 is coupled to the plate 54 at a fixed spacing from at least one of the first and second lumens 60, 62, and since the suturing device is now pivotable via the follower 48 on the guide 64, the suturing device may then be used to place a stitch of the second implant suture 88 into the tissue at a position determined at least in part by an arc which the minimally invasive suturing device is able to follow by having the follower 48 pivot on the guide 64. An echocardiogram can help determine the best position for the stitch of the second implant suture relative to the annulus, and the surgeon has the confidence of a reliable spacing relative to the previous implant suture thanks to the novel suture placement system and follower disclosed herein. Although not illustrated herein, the second implant suture 88 may be part of another suture placement system so that the process may be repeated as desired until a series of stitches have been placed around the tricuspid annulus. This system and method enables reliable, repeatably spaced stitches to be placed in a blood field where direct or endoscopic visualization is not possible.

Figure 5A:
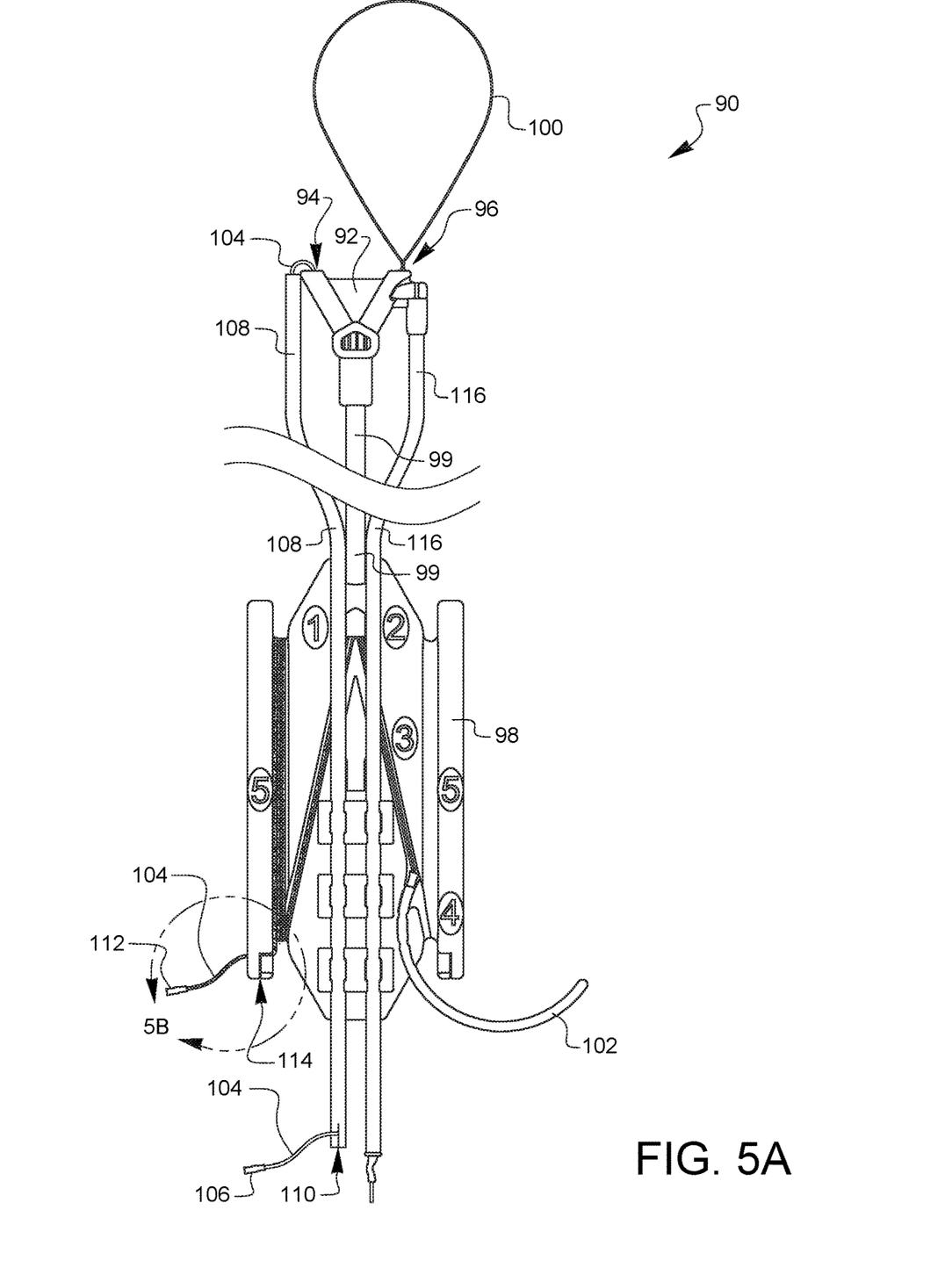
FIG. 5A illustrates another embodiment of a suture placement system.
Figure 5B:
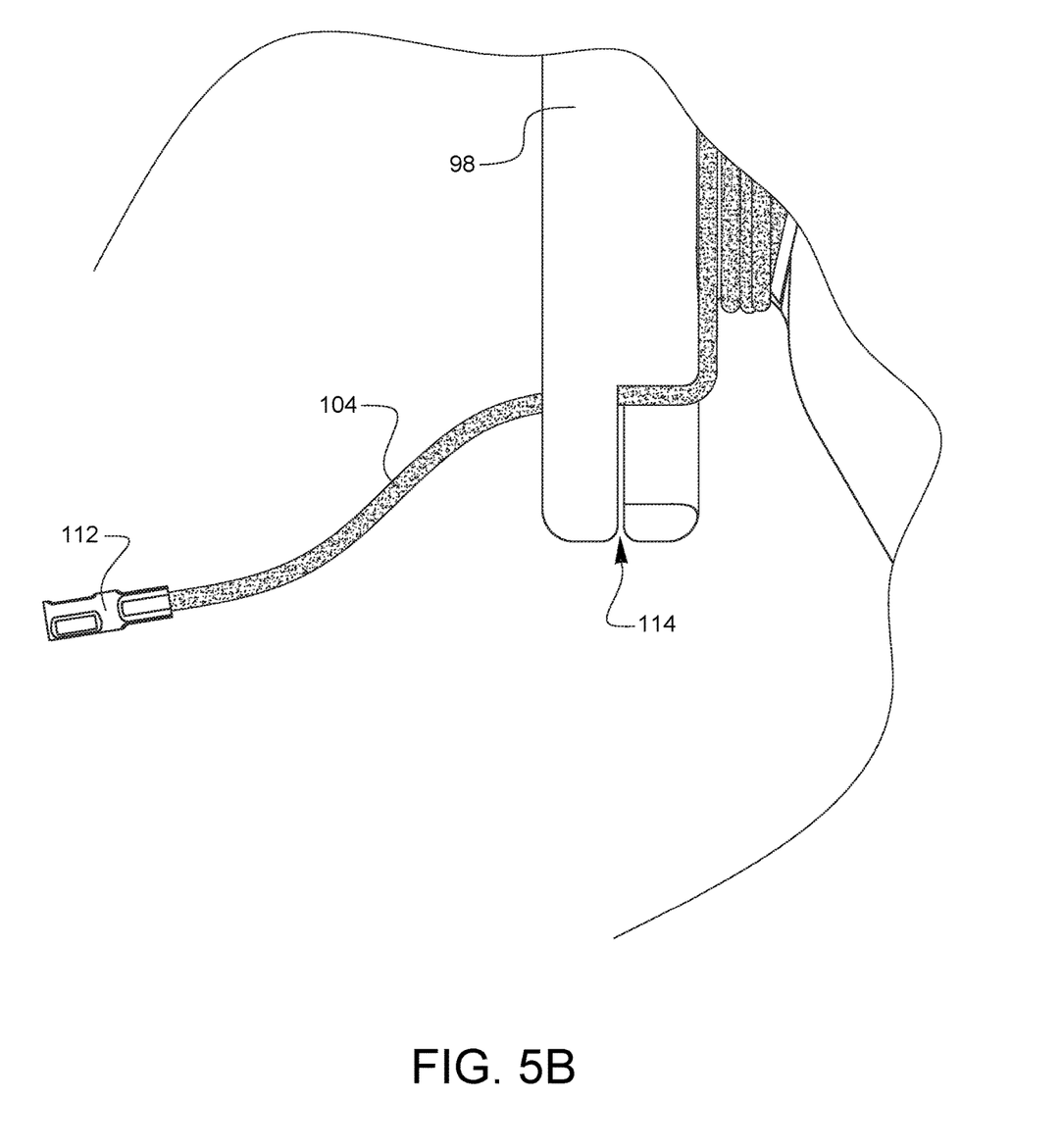
FIG. 5B is an enlarged view of a portion of a holder (from the suture placement system of FIG. 5A) where the end of an implant suture with a ferrule is held.

FIG. 5A illustrates another embodiment of a suture placement system 90. In this embodiment, the plate 92 has been formed from a molded piece which has bifurcated channels which form the first and second lumen openings 94, 96 on the distal side. Proximally, a holder 98 is provided coupled to the first and second lumens (which are housed in a single tube 99 as they join the holder 98). The snare loop 100 extends distally from one of the openings 96 as with the above embodiments. The snare handle 102 extends proximally from the tube 99 and is available near the holder 98. The implant suture 104 extends from the other opening 94 in the plate 92, and the end with the first ferrule 106 is further passed through a suture organization tube 108 which clips into the holder 98. The end of the implant suture 104 which extends from the suture organization tube 108 near the holder 98 has the first ferrule 106. This end of the suture 106 is also colored white in this embodiment. The suture organization tube 108 also has a slit 110 which is configured to hold the implant suture 104 so that it does not pass back into the suture organization tube 108. The end of the implant suture 104 with the second ferrule 112 extends from proximal end of the tube 99 with the two lumens. This end of the implant suture 104 is colored differently from the white color to differentiate from the other end, and is wrapped around the holder 98 and secured to the holder on a securing feature 114 until the user removes the end of the implant suture 104 with the second ferrule 112. The guide tube 116 is also clipped into the holder 98. FIG. 5B is an enlarged view of a portion of the holder 98 where the end of the suture 104 with the second ferrule 112 is held.

Figure 6:
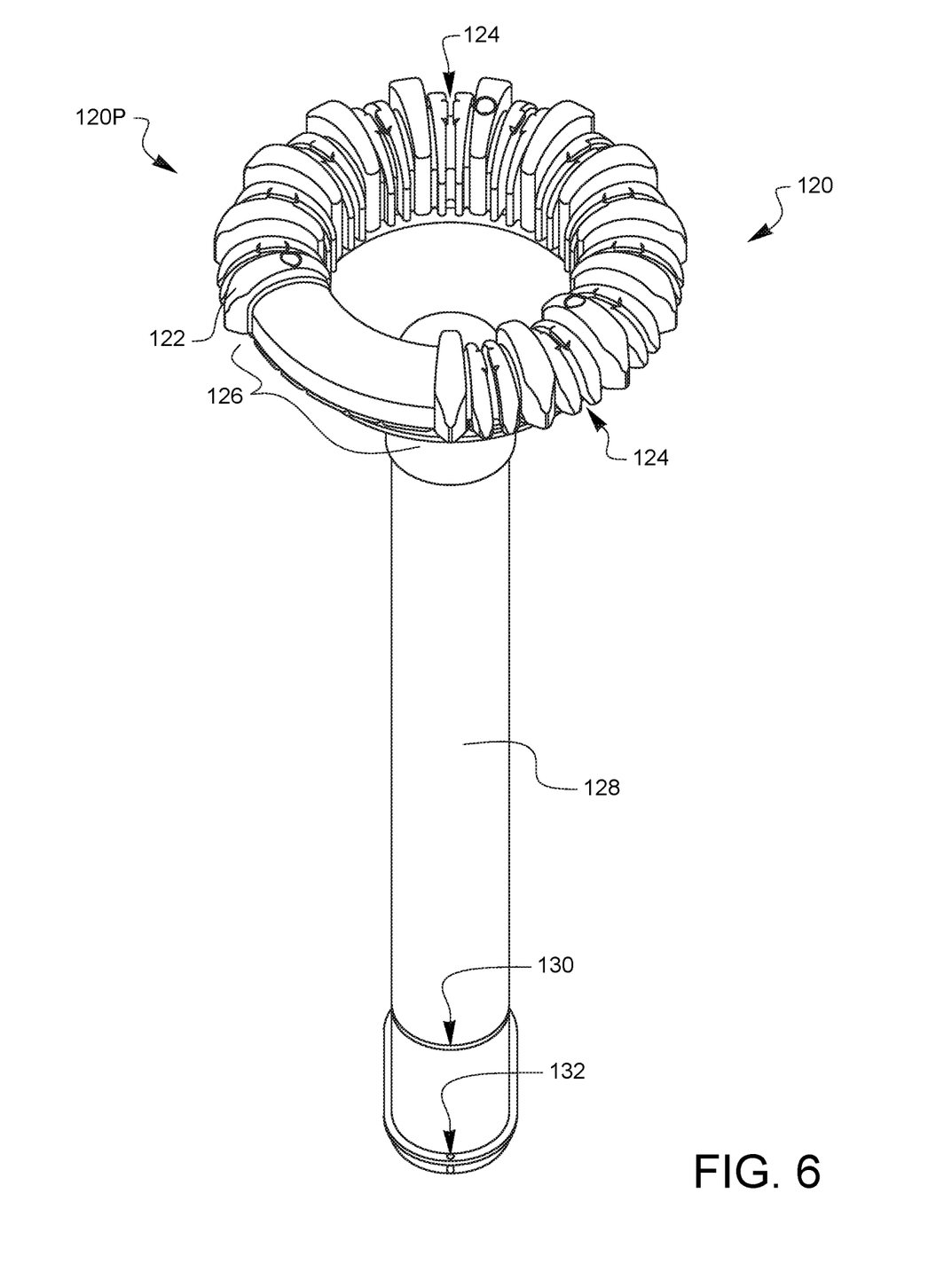
FIG. 6 illustrates one embodiment of an atrial cannula which may be used in conjunction with a minimally invasive suturing device such as, but not limited to the device of FIG. 1A in conjunction with the suture placement systems of FIG. 2 or FIG. 5A.

A right atrial cannula 120 may be provided for intercostal access to the right atrium of the heart while the heart is beating. An embodiment of such a cannula 120 is illustrated in FIG. 6. This cannula can be used in conjunction with a minimally invasive suturing device such as, but not limited to the device 30 of FIG. 1A in conjunction with the suture placement systems 52, 90 described above. On a proximal end 120P, the cannula 120 has an organization template 122 around the circumference of the cannula 120. The organization template 122 has tube management grooves 124 around a portion of the circumference in which one or more tubes from the suture placement device may be mounted. A section 126 of the organization template 122 is devoid of tube management grooves 124, and this corresponds to a portion of the tricuspid valve which should not be sutured, so that needles do not pierce vital segments of the heart's conduction path. This visual reminder on the organization template 124 may be a helpful reminder for surgeons. The cannula 120 has a riser tube 128 which is sized to allow the cannula 120 to reach an incision in the right atrium, but which is long enough so that the slightly pressurized blood passing through the right atrium during this beating heart procedure does not rise above and out of the cannula. The distal end of the cannula has a groove 130 to which a pursestring suture placed into the heart at the incision point may be tied to secure the heart tissue to the cannula 120. The base of the cannula also has holes 132 through which guide sutures may be threaded to help pass the cannula 120 into position on a beating heart.

Figure 7:
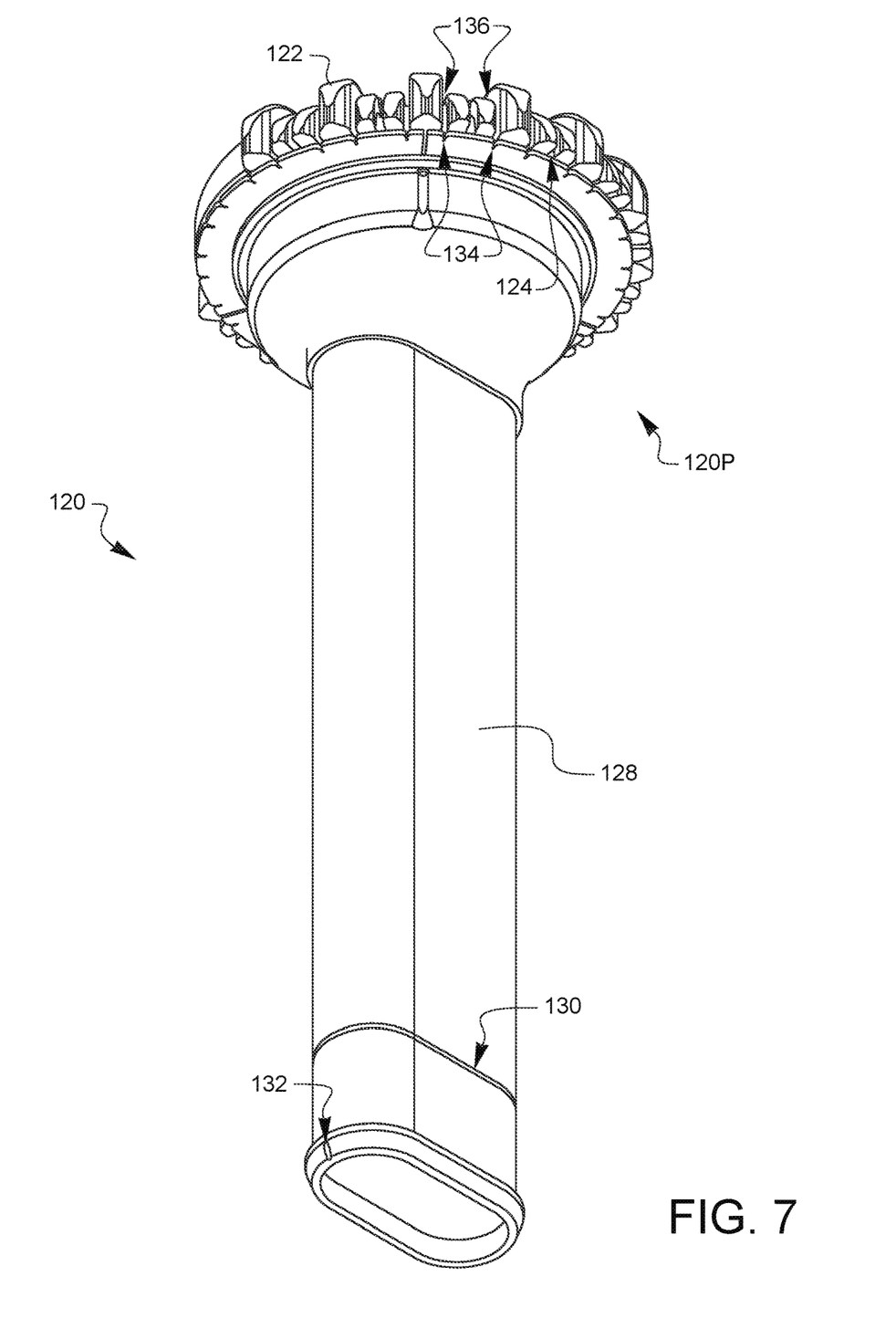
FIG. 7 illustrates the underside of a proximal end of the cannula of FIG. 6.

FIG. 7 illustrates the underside of the proximal end 120P of the cannula 120, where it can be seen that there are suture pinching slots 134 underneath the organization template 122. Each of the suture pinching slots align with a corresponding suture channel 136 in the organization template 122. The suture channels 136 are interspersed with the tube management grooves in this embodiment. In other embodiments, the suture channels and the tube management grooves may coincide to offer users more options. Sutures passing through the cannula 120 may be wrapped around the suture channels 136 and then pulled into a corresponding suture pinching slot 134 for holding various sutures if desired.

Figure 8:
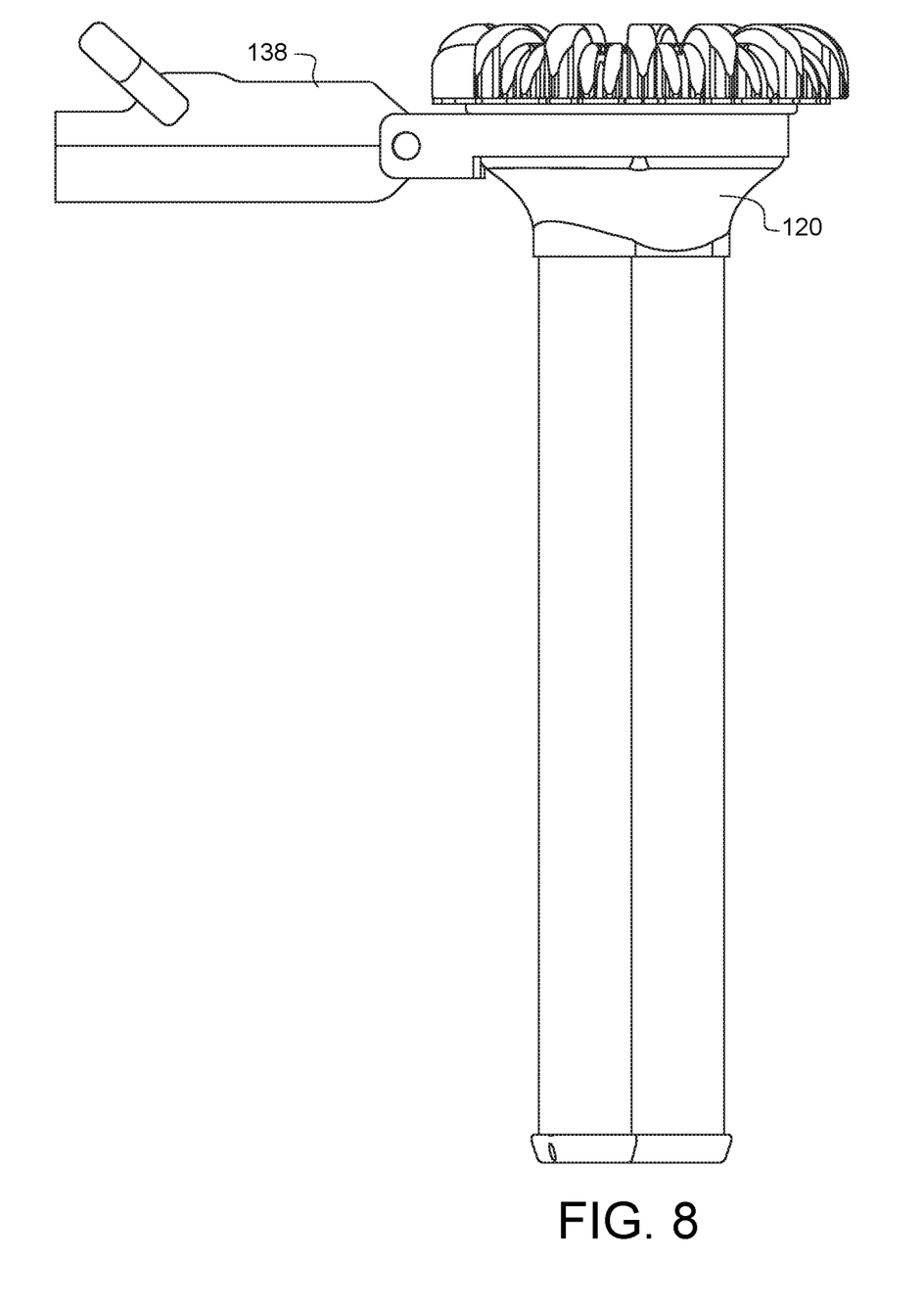
FIG. 8 illustrates an embodiment where the cannula of FIG. 7 has an optional adapter for coupling to a stabilization arm.

FIG. 8 illustrates an embodiment where the cannula 120 of FIG. 7 has an optional adapter 138 for coupling to a stabilization arm (not shown), such as, for example, the miniARM™ instrument holder available from LSI Solutions, Inc., Victor, N.Y. (www.lsisolutions.com). Other embodiments may have other types of adapters for coupling to other types of stabilization arms.

Various advantages of a minimally invasive suture placement system and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A cannula, comprising:
a riser tube having a proximal end and a distal end; and
a circumferential organization template coupled to the proximal end of the riser tube, the circumferential organization template comprising:
a plurality of suture pinching slots formed on an outer perimeter edge of a base member disposed on an underside of the circumferential organization template;
a plurality of tube management grooves positioned around the circumferential organization template; and
a plurality of suture channels positioned around the circumferential organization template, wherein each of the plurality of suture channels is configured to receive a first portion of a suture and each of the plurality of suture pinching slots is configured to receive a second portion of the suture,
wherein the circumferential organization template comprises (a) a plurality of a first type of projection that each extends proximally a first distance from the base member and (b) a plurality of a second type of projection that each extends proximally a second distance from the base member, and wherein the second distance is greater than the first distance, and
wherein each of the plurality of suture channels are defined by a first gap formed between a corresponding one of the plurality of the first type of projection and a corresponding one of the plurality of the second type of projection, wherein the corresponding one of the plurality of first type of projection is adjacent to the corresponding one of the plurality of the second type of projection.

2. The cannula of claim 1, the circumferential organization template further comprising a portion of the circumferential organization template devoid of tube management grooves.

3. The cannula of claim 1, the circumferential organization template further comprising a portion of the circumferential organization template devoid of suture channels.

4. The cannula of claim 1, wherein each of the plurality of suture channels are aligned with each of the plurality of suture pinching slots.

5. The cannula of claim 1, wherein the riser tube is sized to reach an incision in a right atrium.

6. The cannula of claim 1, further comprising a groove at the distal end of the riser tube.

7. The cannula of claim 1, further comprising a hole at the distal end of the riser tube.

8. The cannula of claim 1, further comprising an adapter coupled to the proximal end of the riser tube.

9. The cannula of claim 1, wherein the plurality of tube management grooves and the plurality of suture channels are each radially arrayed around the base member.

10. The cannula of claim 1, wherein each of the plurality of tube management grooves are defined by a second gap formed between a first one of the plurality of the first type of projection and a second one of the plurality of the first type of projection, wherein the first one of the plurality of the first type of projection is adjacent to the second one of the plurality of the first type of projection.

11. The cannula of claim 1, wherein the base member is an annular ring disposed on the underside of the circumferential organization template.

12. The cannula of claim 11, wherein the annular ring is planar.

* * * * *